(12) United States Patent
Giordano et al.

(10) Patent No.: US 8,760,659 B2
(45) Date of Patent: Jun. 24, 2014

(54) TURBIDITY SENSOR FOR AN ELECTRIC HOUSEHOLD APPLIANCE

(75) Inventors: Sergio Giordano, Caselle (IT); Domenico Pietrafesa, San Mauro Torinese (IT)

(73) Assignee: Illinois Tool Works Inc., Glenview, IL (US)

( * ) Notice: Subject to any disclaimer, the term of this patent is extended or adjusted under 35 U.S.C. 154(b) by 224 days.

(21) Appl. No.: 13/254,948

(22) PCT Filed: Mar. 5, 2010

(86) PCT No.: PCT/US2010/026299
§ 371 (c)(1),
(2), (4) Date: Sep. 6, 2011

(87) PCT Pub. No.: WO2010/102166
PCT Pub. Date: Sep. 10, 2010

(65) Prior Publication Data
US 2012/0002206 A1    Jan. 5, 2012

(30) Foreign Application Priority Data
Mar. 6, 2009 (IT) .............................. TO2009A0168

(51) Int. Cl.
*G01N 21/00* (2006.01)

(52) U.S. Cl.
USPC ........................................................ 356/441

(58) Field of Classification Search
None
See application file for complete search history.

(56) References Cited

U.S. PATENT DOCUMENTS

| 2,649,011 | A | | 8/1953 | Black |
| 5,444,531 | A | * | 8/1995 | Foreman et al. ............... 356/341 |
| 6,678,045 | B2 | * | 1/2004 | Rettig et al. ................... 356/338 |
| 6,842,243 | B2 | * | 1/2005 | Tokhtuev et al. .............. 356/338 |
| 6,894,778 | B2 | * | 5/2005 | Palumbo et al. ............... 356/338 |
| 7,142,299 | B2 | * | 11/2006 | Tokhtuev et al. .............. 356/338 |
| 7,397,564 | B2 | * | 7/2008 | Diez Garcia et al. .......... 356/440 |
| 7,659,980 | B1 | * | 2/2010 | Mitchell et al. ............... 356/339 |
| 2003/0142316 | A1 | | 7/2003 | Schenkl et al. |
| 2007/0046942 | A1 | | 3/2007 | Ng et al. |

FOREIGN PATENT DOCUMENTS

| CN | 1576823 A | 2/2005 |
| DE | 2559806 B1 | 1/1980 |
| DE | 3151504 A1 * | 7/1983 |

(Continued)

OTHER PUBLICATIONS

ISR for PCT/US2010/026299 dated Apr. 9, 2010.

(Continued)

*Primary Examiner* — Gordon J Stock, Jr.
(74) *Attorney, Agent, or Firm* — Lowe Hauptman & Ham LLP

(57) ABSTRACT

An optical-type turbidity sensor including a casing accommodating photo emitting means and photo receiving means therein, wherein the photo emitting means and the photo receiving means are arranged side-by-side on a same side of the casing, preferably underneath a same lens-shaped, transparent portion of the same, and are facing to, and spaced from, a reflecting surface carried by the casing and adapted to receive a light radiation from the photo emitting means for reflecting it towards the photo receiving means; the reflecting surface is operatively associated with means for varying a distance existing between the reflecting surface and the side of the casing provided with the photo emitting and photo receiving means arranged side-by-side.

12 Claims, 1 Drawing Sheet

(56) References Cited

FOREIGN PATENT DOCUMENTS

| DE | 19714695 | A1 | 10/1998 |
| EP | 0178031 | A1 | 4/1986 |
| EP | 1335060 | A1 | 8/2003 |

OTHER PUBLICATIONS

Search report results for Italian Application No. TO2009A000168 dated Oct. 6, 2009.

* cited by examiner

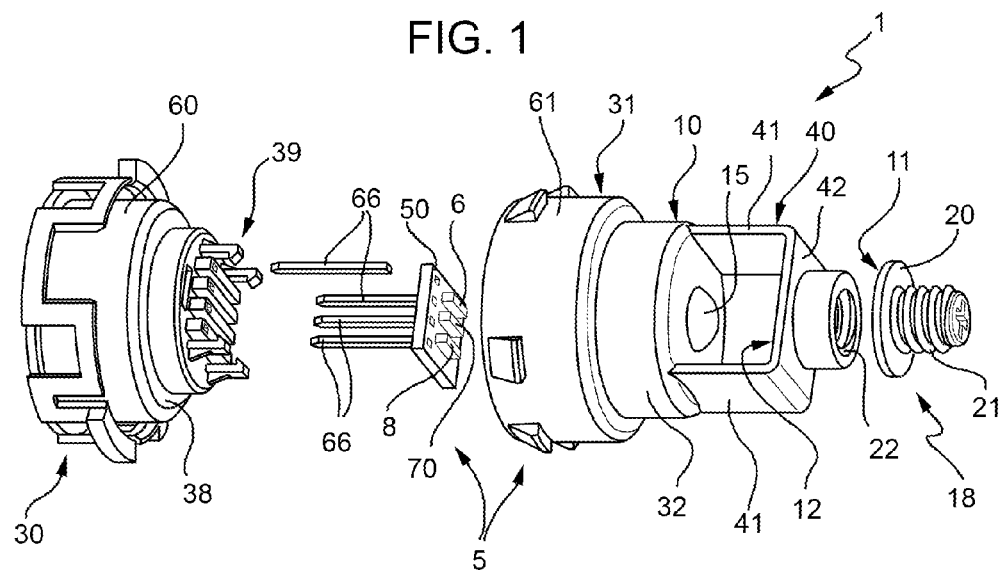
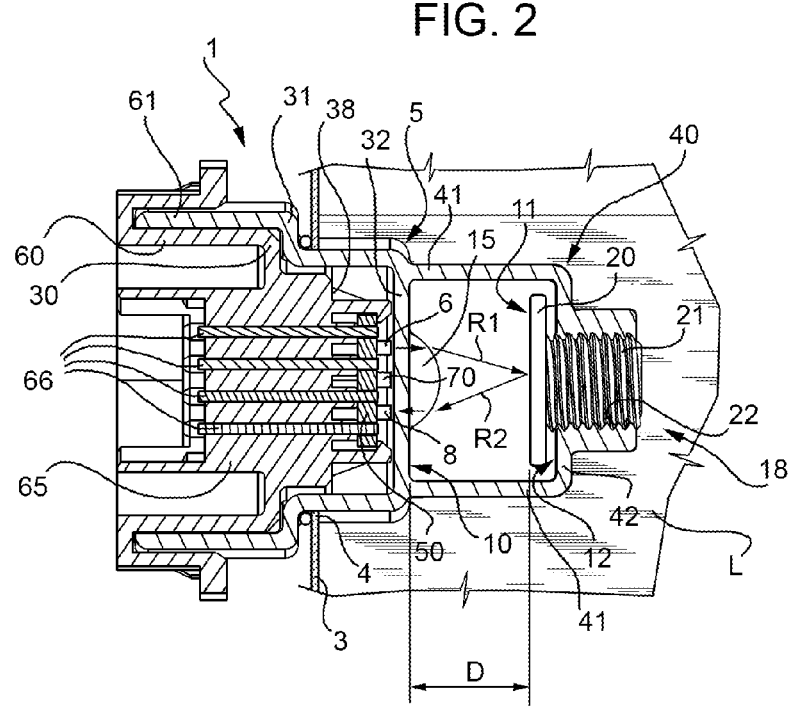

TURBIDITY SENSOR FOR AN ELECTRIC HOUSEHOLD APPLIANCE

RELATED APPLICATIONS

The present application is national phase of PCT/US2010/026299 filed Mar. 5, 2010, and claims priority from Italian Application No. TO2009A000168, filed Mar. 6, 2009.

TECHNICAL FIELD

The present invention relates to an optical-type turbidity sensor for an electric household appliance, in particular for a washing machine or dishwasher, aimed at, when the electric household appliance is running, allowing to measure the optical absorbance of the liquid present in a tank of the electric household appliance, e.g. in the basket of a washing machine or in the sump of a dishwasher.

BACKGROUND ART

An optical-type sensor is known from EP 133506081, which allows to detect in use the turbidity of a washing fluid in an electric household appliance by means of optical absorbance measures. Such measures are used by the electric household appliance to check the correct performance of the set washing cycle and/or to adapt the washing cycle to the dirt conditions of dishes or laundry being washed.

The known sensor has a fork-shaped casing with two "fingers", a first one accommodating a photo emitting element at the tip, and the second one accommodating a photo receiving element; furthermore, a temperature sensor is also provided on the longest "finger". The two photo emitting and photo receiving elements thus allow to measure the absorbance of a fluid between the two "fingers", in order to evaluate the turbidity of the fluid itself.

The known sensor has several drawbacks. Firstly, it is rather large in size, especially in the transversal direction. Secondly, it does not allow any sensor reading calibration except at the electronic level, e.g. using a microprocessor, which is a costly and complex solution. Thirdly, the distance between emitter and receiver may be influenced by possible deformations of the "fingers" which may occur in use, thus compromising the sensor accuracy. It is also complex to be assembled on the electric household appliance due to the prismatic shape of the casing.

DISCLOSURE OF INVENTION

It is an object of the present invention to overcome the drawbacks of the prior art, providing a turbidity sensor having small dimensions, high reliability, high assembly ease and high manufacturing ease, which may reduce costs, and which may further be easily calibrated.

The present invention thus relates to a turbidity sensor for an electric household appliance, as defined in claim 1.

In particular, the sensor comprises a casing accommodating photo emitting means and photo receiving means therein; according to the main aspect of the invention, the photo emitting means and the photo receiving means are arranged side-by-side on a same first side of the casing facing to, and spaced from, a reflecting surface carried by a second side of the casing opposite to the first and adapted to receive a radiation from the photo emitting means for reflecting it towards the photo receiving means.

According to a further aspect of the invention, the reflecting surface is operatively associated with means, in particular screw means, for micrometrically varying the distance between the reflecting surface and the first side of the casing. Furthermore, the photo emitting and the photo receiving means are arranged underneath the same lens-shaped, transparent portion of the first side of the casing.

Thereby, it has been experimentally found that, as the absorbance readings are carried out by reflection, they are much more accurate than the "direct" readings carried out by a light receiver which directly receives the radiation emitted by the light emitter. Moreover, by micrometrically varying the distance between the reflecting surface and the lens which covers the emitting and receiving diodes, which may be simply and cost-effectively obtained by fitting the reflecting surface on a threaded shank, a mechanical calibration of the sensor may be carried out very simply. Another advantage is that since all the electronic components are adjacent to one another, they may be obtained on a single printed circuit, which may further carry a temperature detecting element.

Finally, the casing may be made with axial symmetry by means of cup-shaped elements concentrically coupled on the side of their respective concavities, thus strongly reducing the dimensions of the sensor and facilitating the fluid tight assembly thereof in the operative seat through the tank of the electric household appliance.

BRIEF DESCRIPTION OF THE DRAWINGS

Further features and advantages of the present invention will be apparent from the following description of a preferred embodiment, merely provided by way of non-limitative example, with reference to the accompanying drawing, in which:

FIG. 1 shows an axonometric, three-quarters front view in an exploded configuration of a turbidity sensor according to the invention; and FIG. 2 shows a sectioned longitudinal view of the sensor in FIG. 1 in the assembled configuration.

BEST MODE FOR CARRYING OUT THE INVENTION

With reference to FIGS. 1 and 2, numeral 1 indicates as a whole an optical-type turbidity sensor for an electric household appliance, typically a washing machine or dishwasher, of which only a tank 3 is shown, provided with a through seat 4 for the sensor 1 and in use full of an operating liquid or fluid L of the electric household appliance, the physical features of which, such as optical absorbance and temperature, are intended to be measured.

Sensor 1 comprises a casing 5 accommodating photo emitting means, consisting of a diode 6, and photo receiving means, consisting of a separate diode 8 therein.

According to an aspect of the invention, the photo emitting means 6 and the photo receiving means 8 are arranged side-by-side on a same first side 10 of the casing 5 facing to, and spaced from, a reflecting surface 11 carried by a second side 12 of the casing 5 opposite to the first. The reflecting surface 11 is adapted to receive a radiation R1 (e.g. light or infrared radiation) from the photo emitting means 6 and reflect it, as a reflecting radiation R2, towards the photo receiving means 8.

In particular, the photo emitting and the photo receiving means 6,8 are arranged side-by-side underneath the same lens-shaped, transparent portion 15 of the first side 10 of the casing 5.

Moreover, according to a further preferred aspect of the invention, the reflecting surface 11 is operatively associated with means 18 for micrometrically varying a distance D existing between the reflecting surface 11 and the first side 10 of the casing 5. These means 18 are screw means as the reflecting surface 11 is obtained on one face of a disc 20 carried by a threaded shank 21, which is in turn coupled with a threaded seat 22 obtained through the second side 12 of the casing 5.

According to a further preferred aspect of the invention, casing 5 comprises first and second cup-shaped elements, indicated by numerals 30 and 31 respectively, which cup-shaped element 30 is concentrically fitted within cup-shaped element 31, with their respective concavities facing a same side; a bottom wall 32 of the cup-shaped element 31 defines the first side 10 of casing 5 with a first external face thereof and is provided, on the side opposite to first cup-shaped element 30, with a rectangular frame 40 consisting of at least one pair of opposite side members 41 carrying, at a predetermined distance from the bottom wall 32, and in a position facing the same, a bridge member 42 defining the second side 12 of casing 5.

Diodes 6 and 8 are carried side-by-side on a same face of a printed circuit 50, sandwiched between the bottom wall 32 of the cup-shaped element 31 and a corresponding bottom wall 38 of the cup-shaped element 30, provided for this purpose with a snapping support 39 for the printed circuit 50.

The cup-shaped elements 30 and 31 are made of synthetic plastic material and are reciprocally and integrally snap-coupled by means of their respective side walls 60,61; a connector 65 is further obtained in one piece within the concavity of the first cup-shaped element 30, being connected to the printed circuit 50 by means of a plurality of electrically conductive shanks or rods 66 driven into the printed circuit 50 in appropriate perforations thereof and mounted through the first cup-shaped element 30.

Finally, according to another aspect of the invention, a temperature detecting element 70 is also provided by the side of the photo emitting and photo receiving means 6,8 on the side 10 of casing 5. In particular, the photo emitting and photo receiving means 6,8 and the temperature detecting element 70 are carried by the same printed circuit 50, which is arranged in use underneath the lens-shaped, transparent portion 15.

Alternatively, according to a variant (not shown), instead of two separate diodes 6 and 8, a single diode may be used which, in this case, will be arranged by the side of the temperature-sensitive element 70, the single diode acting both as light emitter and light receiver; in this case, the lens 15 should be made so as to focus the reflected rays R2 towards the single diode.

The invention claimed is:

1. An optical turbidity sensor comprising
a casing accommodating photo emitting means and photo receiving means therein; wherein the photo emitting means and the photo receiving means are arranged side-by-side on a same first side of the casing facing to, and spaced from, a reflecting surface carried by a second side of the casing opposite the first side and adapted to receive a radiation from the photo emitting means for reflecting the radiation towards the photo receiving means, wherein said casing comprises first and second substantially cylindrical elements, concentrically fitted the first substantially cylindrical element within the second substantially cylindrical element, the respective concavities facing a same direction; a bottom wall of the second substantially cylindrical element defining said first side of the casing and being provided, on a side opposite to the first substantially cylindrical element, with a frame consisting of at least one pair of opposite side members carrying, at a predetermined distance apart from said bottom wall and in a position facing the same first side of the casing, a bridge member defining the second side of the casing.

2. A sensor according to claim 1, wherein said photo emitting means and photo receiving means are arranged side-by-side underneath a same transparent portion of said first side of the casing.

3. A sensor according to claim 1, wherein said reflecting surface is operatively associated with means for micrometrically varying the distance existing between the reflecting surface and the first side of the casing.

4. A sensor according to claim 1, wherein said photo emitting and photo receiving means consist of respective diodes carried side-by-side on a same face of a printed circuit sandwiched between the bottom wall of the second substantially cylindrical element and a corresponding bottom wall of the first substantially cylindrical element.

5. A sensor according to claim 1, wherein a temperature detecting element is also provided by a side of said photo emitting and photo receiving means on said first side of the casing.

6. A sensor according to claim 3, wherein said means for varying the distance between the reflecting surface and the first side of the casing are screw means; the reflecting surface being obtained on a face of a disc carried by a threaded shank, which is coupled with a threaded seat obtained through the second side of the casing.

7. A sensor according to claim 4, wherein said first and second substantially cylindrical elements are made of a synthetic plastic material and are reciprocally and integrally snap-coupled by means of their respective side walls; a connector connected to said printed circuit by means of a plurality of electrically conductive shanks driven into the printed circuit and mounted through the first substantially cylindrical element being formed integrally in one piece within the concavity of the first substantially cylindrical element.

8. A sensor according to claim 5, wherein said photo emitting and photo receiving means and said temperature detecting element are carried by a same printed circuit arranged underneath a transparent portion of the first side of casing.

9. An optical turbidity sensor, comprising:
a casing accommodating photo emitting means and photo receiving means therein; wherein the photo emitting means and the photo receiving means are arranged side-by-side on a same first side of the casing facing to, and spaced from, a reflecting surface carried by a second side of the casing opposite the first side and adapted to receive a radiation from the photo emitting means for reflecting the radiation towards the photo receiving means, wherein said casing comprises first and second substantially cylindrical elements, concentrically fitted the first substantially cylindrical element within the second substantially cylindrical element, the respective concavities facing a same direction.

10. A sensor according to claim 9, wherein said photo emitting means and photo receiving means are arranged side-by-side underneath a same transparent portion of said first side of the casing.

11. A sensor according to claim 10, wherein said reflecting surface is operatively associated with means for micrometrically varying the distance existing between the reflecting surface and the first side of the casing.

12. A sensor according to claim 11, wherein said means for varying the distance between the reflecting surface and the first side of the casing are screw means; the reflecting surface being obtained on a face of a disc carried by a threaded shank, which is coupled with a threaded seat obtained through the second side of the casing.

* * * * *